US00PP29030P3

(12) United States Plant Patent
Barnes

(10) Patent No.: US PP29,030 P3
(45) Date of Patent: Feb. 27, 2018

(54) ***CALIBRACHOA* PLANT NAMED 'BBCAL27801'**

(50) Latin Name: ***Calibrachoa* sp.**
Varietal Denomination: BBCAL27801

(71) Applicant: Brent D. Barnes, Riverside, CA (US)

(72) Inventor: Brent D. Barnes, Riverside, CA (US)

(73) Assignee: Plant 21 LLC, Bonsall, CA (US)

( * ) Notice: Subject to any disclaimer, the term of this patent is extended or adjusted under 35 U.S.C. 154(b) by 47 days.

(21) Appl. No.: 14/999,773

(22) Filed: Jun. 24, 2016

(65) Prior Publication Data

US 2017/0374785 P1 Dec. 28, 2017

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Keith O Robinson
(74) *Attorney, Agent, or Firm* — C. A. Whealy

(57) ABSTRACT

A new and distinct *Calibrachoa* plant named 'BBCAL27801', characterized by its upright to outwardly spreading and mounding to eventually trailing plant habit; moderately vigorous to vigorous growth habit; freely branching habit; dense and bushy appearance; freely flowering habit; light purple and dark purple-colored petals with a central yellow-colored star-shaped pattern; and good garden performance.

1 Drawing Sheet

Botanical designation: *Calibrachoa* sp.
Cultivar denomination: 'BBCAL27801'.

BACKGROUND OF THE INVENTION

The present invention relates to a new and distinct cultivar of *Calibrachoa* plant, botanically known as *Calibrachoa* sp. and hereinafter referred to by the name 'BBCAL27801'.

The new *Calibrachoa* plant is a product of a planned breeding program conducted by the Inventor in Bonsall, Calif. The objective of the breeding program is to create new uniform and freely-branching *Calibrachoa* plants with unique and attractive flower coloration and good garden performance.

The new *Calibrachoa* plant originated from a cross-pollination conducted by the Inventor in Bonsall, Calif. on Nov. 13, 2013 of a proprietary seedling selection of *Calibrachoa* sp. identified as code number 12C363-02, not patented, as the female, or seed, parent with a proprietary selection of *Calibrachoa* sp. identified as code number 12C464-14, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jul. 2, 2014.

Asexual reproduction of the new *Calibrachoa* plant by vegetative terminal cuttings in a controlled greenhouse environment in Bonsall, Calif. since Jul. 2, 2014 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBCAL27801'. These characteristics in combination distinguish 'BBCAL27801' as a new and distinct *Calibrachoa* plant:

1. Upright to outwardly spreading and mounding to eventually trailing plant habit.
2. Moderately vigorous to vigorous growth habit.
3. Freely branching habit; dense and bushy appearance.
4. Freely flowering habit.
5. Light purple and dark purple-colored petals with a central yellow-colored star-shaped pattern.
6. Good garden performance.

The new *Calibrachoa* plant can be compared to plants of the female parent selection. Plants of the new *Calibrachoa* differ primarily from plants of the female parent selection in flower color as plants of the female parent selection have pink-colored petals without a central star-shaped pattern.

The new *Calibrachoa* plant can be compared to plants of the male parent selection. Plants of the new *Calibrachoa* differ primarily from plants of the male parent selection in flower color as plants of the male parent selection have light purple and red-colored petals with a central star-shaped pattern that extends to the edge of the petal. In addition, plants of the new *Calibrachoa* are more freely branching than plants of the male parent selection.

Plants of the new *Calibrachoa* can be compared to plants of the *Calibrachoa* sp. 'USCAL91001', disclosed in U.S. Plant Pat. No. 23,232. In side-by-side comparisons, plants of the new *Calibrachoa* differ primarily from plants of 'USCAL91001' in flower color as plants of 'USCAL91001' have red purple-colored flowers with a yellow-colored star pattern that extends to the edge of the petal.

Plants of the new *Calibrachoa* can also be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in flower color as plants of 'USCALI11' have light red purple-colored flowers without a star pattern.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'BBCAL27801' grown in a container.

The photograph at the top of the sheet is a close-up view of a typical flowering plant of 'BBCAL27801'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Calibrachoa* production. During the production of the plants, day and night temperatures ranged from 18° C. to 30° C. Plants were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'BBCAL27801'.

Parentage:

- *Female, or seed, parent*.—Proprietary selection of *Calibrachoa* sp. identified as code number 12C363-02, not patented.
- *Male, or pollen, parent*.—Proprietary selection of *Calibrachoa* sp. identified as code number 12C464-14, not patented.

Propagation:

- *Type*.—By vegetative terminal cuttings.
- *Time to initiate roots, summer*.—About four days at temperatures ranging from 17° C. to 29° C.
- *Time to initiate roots, winter*.—About six days at temperatures ranging from 17° C. to 21° C.
- *Time to produce a rooted plant, summer*.—About 22 days at temperatures ranging from 17° C. to 29° C.
- *Time to produce a rooted plant, winter*.—About 25 days at temperatures ranging from 17° C. to 21° C.
- *Root description*.—Medium in thickness, fibrous; typically white in color, actual color of the roots is dependent on substrate composition, water quality, fertilizer type and formulation, substrate temperature and physiological age of roots.
- *Rooting habit*.—Freely branching; medium density.

Plant description:

- *Plant and growth habit*.—Upright to outwardly spreading and mounding to eventually trailing plant habit; moderately vigorous to vigorous growth habit; moderate growth rate; freely branching habit with about four primary lateral branches each with about three to five secondary branches; dense and bushy appearance.
- *Plant height*.—About 15.2 cm.
- *Plant diameter*.—About 27 cm by 32 cm.

Lateral branch description:

- *Length*.—About 13.5 cm.
- *Diameter*.—About 1.5 mm.
- *Internode length*.—About 1.5 cm.
- *Strength*.—Strong.
- *Aspect*.—Initially upright then outwardly spreading to eventually trailing.
- *Texture and luster*.—Pubescent; matte.
- *Color, developing*.—Close to 146C.
- *Color, developed*.—Close to 146B.

Leaf description:

- *Arrangement*.—Before flowering, alternate; after flowering, opposite; leaves simple.
- *Length*.—About 3 cm.
- *Width*.—About 1.1 cm.
- *Shape*.—Spatulate to elliptical.
- *Apex*.—Rounded.
- *Base*.—Attenuate.
- *Margin*.—Entire.
- *Texture and luster, upper and lower surfaces*.—Pubescent, minute; matte.
- *Venation pattern*.—Pinnate; arcuate.
- *Color*.—Developing leaves, upper and lower surfaces: Close to 146B. Fully expanded leaves, upper surface: Close to N137A; venation, close to 147B. Fully expanded leaves, lower surface: Close to N137B; venation, close to 147C.
- *Petioles*.—Length: About 5 mm. Diameter: About 2 mm. Texture and luster, upper and lower surfaces: Pubescent, minute; matte. Color, upper and lower surfaces: Close to 146C.

Flower description:

- *Flower type and flowering habit*.—Single salverform flowers arising from leaf axils; freely flowering habit with typically about 185 flowers and flower buds developing per plant; flowers face upright to outwardly.
- *Fragrance*.—None detected.
- *Natural flowering season*.—Plants of the new *Calibrachoa* begin flowering about six weeks after planting; plants flower continuously from the spring though the summer until frost.
- *Flower longevity*.—Individual flowers last about one week on the plant; flowers persistent.
- *Flower buds*.—Length: About 2.5 cm. Diameter: About 7 mm. Shape: Oblong, elongate. Texture and luster: Pubescent, minute; matte. Color: Close to 76D.
- *Flower diameter*.—About 2.8 cm by 3.2 cm.
- *Flower length (height)*.—About 2.7 cm.
- *Flower throat diameter*.—About 5 mm by 8 mm.
- *Flower tube length*.—About 2 cm.
- *Flower tube diameter*.—Proximally, about 3 mm; distally, about 7 mm.
- *Corolla*.—Arrangement: Five fused petals opening into a flared trumpet. Petal lobe length (from throat): About 1.2 cm. Petal lobe width: About 1.5 cm. Petal shape: Fan-shaped. Petal apex: Rounded to slightly emarginate. Petal margin: Entire. Petal texture and luster, upper surface: Smooth, glabrous, velvety; matte. Petal texture and luster, lower surface: Pubescent, minute; matte. Throat texture and luster: Smooth, glabrous; matte. Tube texture and luster: Pubescent, minute and primarily along the veins; matte. Color: Petal lobe, when opening, upper surface: Close to 76B to 76C. Petal lobe, when opening, lower surface: Close to 76D. Petal lobe, fully opened, upper surface: Ground color, close to 77A; band surrounding the throat, close to N79A; venation, close to N78A to N78B; with development, ground color becoming closer to 84D and band, closer to 79B. Petal lobe, fully opened, lower surface: Close to 84C; venation, close to N77B to N77C; with development, color becoming closer to 85C. Throat and central star pattern: Close to 9A; venation, close to 197C. Tube: Close to 162D; venation, close to 183A.

*Calyx*.—Arrangement: One star-shaped calyx tube with five sepals fused towards the base and arranged in a single whorl. Length: About 1.5 cm. Diameter: About 1.7 cm. Sepal length: About 1.1 cm. Sepal width: About 2.5 mm. Sepal shape: Lanceolate. Sepal apex: Acute. Sepal margin: Entire. Sepal texture and luster, upper and lower surfaces: Pubescent, minute; matte. Sepal color, upper and lower surfaces: Close to 146A.

*Peduncles*.—Length: About 2.2 cm. Diameter: About 1.5 mm. Angle: About 45° from stem axis. Strength: Strong. Texture and luster: Pubescent, minute; matte. Color: Close to 146B.

*Reproductive organs*.—Stamens: Quantity: Five per flower. Filament length: About 1 cm. Filament color: Close to 145C. Anther size: About 1 mm by 1 mm. Anther shape: Round. Anther color: Close to 6D. Pollen amount: Moderate. Pollen color: Close to 7C. Pistils: Quantity: One per flower. Pistil length: About 1 cm. Style length: About 8 mm. Style color: Close to 145B. Stigma diameter: About 1 mm. Stigma shape: Oval. Stigma color: Close to 144A. Ovary color: Close to 144D. Seeds and fruits: Seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'BBCAL27801' as illustrated and described.

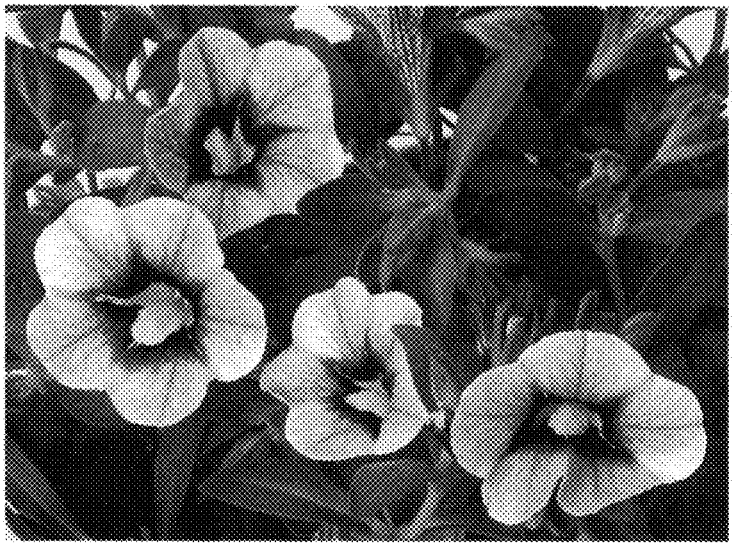
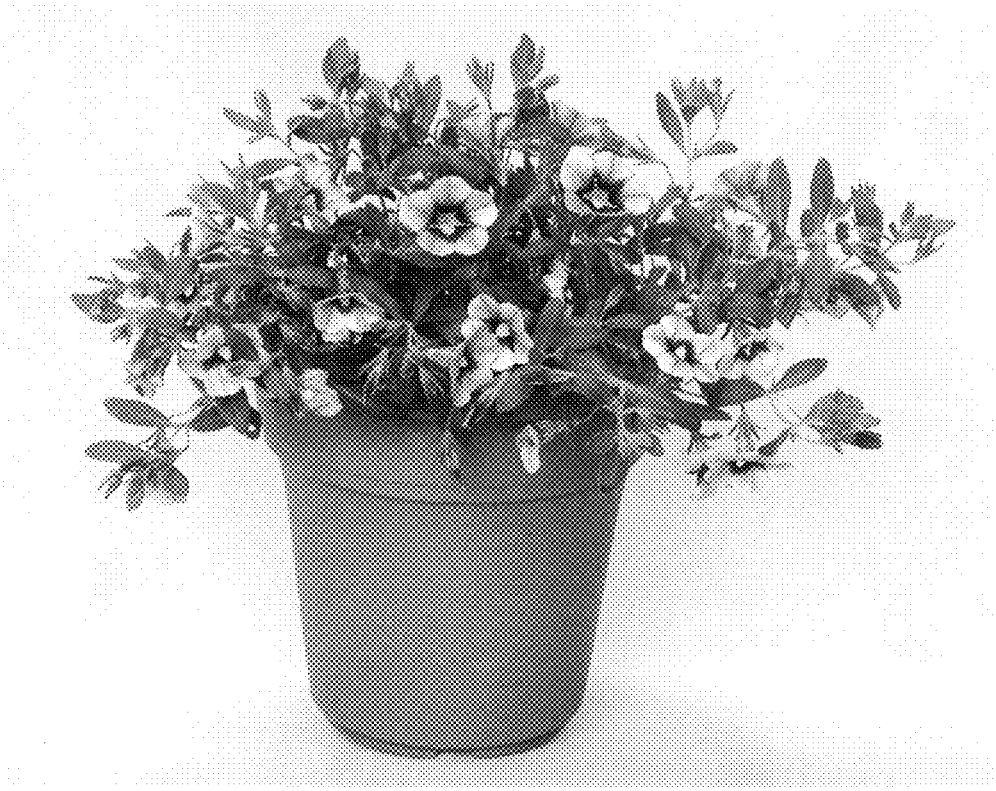

* * * * *